(12) United States Patent
Overstreet

(10) Patent No.: US 7,043,303 B1
(45) Date of Patent: May 9, 2006

(54) ENHANCED METHODS FOR DETERMINING ISO-LOUDNESS CONTOURS FOR FITTING COCHLEAR IMPLANT SOUND PROCESSORS

(75) Inventor: Edward H. Overstreet, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 230 days.

(21) Appl. No.: 10/647,372

(22) Filed: Aug. 25, 2003

Related U.S. Application Data

(60) Provisional application No. 60/407,263, filed on Aug. 30, 2002.

(51) Int. Cl.
*A61N 1/36* (2006.01)

(52) U.S. Cl. .................................................. 607/57

(58) Field of Classification Search .............. 607/55, 607/56, 57, 136, 137, 66
See application file for complete search history.

(56) References Cited

U.S. PATENT DOCUMENTS

| | | | |
|---|---|---|---|
| 3,751,605 A | | 8/1973 | Michelson |
| 4,400,590 A | | 8/1983 | Michelson |
| 4,495,384 A | | 1/1985 | Scott et al. |
| 4,819,647 A | | 4/1989 | Byers et al. |
| 5,597,380 A | * | 1/1997 | McDermott et al. .......... 607/57 |
| 5,603,726 A | | 2/1997 | Schulman et al. |
| 5,626,629 A | | 5/1997 | Faltys et al. |
| 5,938,691 A | | 8/1999 | Schulman et al. |
| 6,067,474 A | | 5/2000 | Schulman et al. |
| 6,078,838 A | | 6/2000 | Rubinstein |
| 6,129,753 A | | 10/2000 | Kuzma |
| 6,157,861 A | * | 12/2000 | Faltys et al. .................. 607/57 |
| 6,195,585 B1 | | 2/2001 | Karunasiri et al. |
| 6,205,360 B1 | * | 3/2001 | Carter et al. .................. 607/57 |
| 6,208,882 B1 | | 3/2001 | Lenarz et al. |
| 6,219,580 B1 | | 4/2001 | Faltys et al. |
| 6,249,704 B1 | | 6/2001 | Maltan et al. |
| 6,289,247 B1 | | 9/2001 | Faltys et al. |
| 6,295,467 B1 | | 9/2001 | Kollmeier et al. |

(Continued)

FOREIGN PATENT DOCUMENTS

WO  WO-03/015863 A2  2/2003

OTHER PUBLICATIONS van Wieringen, et al., "Comparison of Procedures to Determine Electrical Stimulation Thresholds in Cochlear Implant Users", Ear and Hearing, vol. 22(6), (2001), pp. 528-538.

(Continued)

*Primary Examiner*—Jeffrey R. Jastrzab
*Assistant Examiner*—Alyssa M. Alter
(74) *Attorney, Agent, or Firm*—Laura Haburay Bishop; Philip H. Lee

(57) ABSTRACT

Methods are taught to simplify the cochlear implant fitting process for various cochlear prostheses and stimulation strategies, including high rate stimulation strategies. For instance, patient self-programming is made possible. In addition, auto-fitting is made possible (particularly useful for very young patients and other patients for whom it is challenging to obtain feedback) using iso-neural response contours which can be linearly transposed to arrive at iso-loudness contours. Furthermore, M iso-loudness contours (or iso-neural contours) can be linearly transposed to determine T iso-loudness contours. In addition, wider pulse widths can be used to generate an iso-loudness contour whose shape can be used (via linear transposition) to program high-rate, narrow pulse width stimulation.

20 Claims, 10 Drawing Sheets

U.S. PATENT DOCUMENTS 6,415,185 B1    7/2002   Maltan
6,778,858 B1 *  8/2004   Peeters .................. 607/57

OTHER PUBLICATIONS

Overstreet and Faltys inventors for AB-254U; U.S. Appl. No. 10/218,645; filed Aug. 13, 2002; entitled "Cochlear Implant and Simplified Method for Fitting Same".

Faltys inventor for AB-257U; U.S. Appl. No. 10/218,616; filed Aug. 13, 2002; entitled "Bionic Ear Programming System".

Segel, Overstreet, Kruger, and Mishra inventors for AB-313U; U.S. Appl. No. 10/651,653; filed Aug. 29, 2003; entitled System and Method for Fitting a Cochlear Implant Sound Processor Using Alternative Signals.

Rubinstein et al., "The Neurophysiological Effects of Simulated Auditory Prosthesis Simulation" Second Quarterly Progress Report NO1-DC-6-2111.

Zeng, et al., "Loudness of Simple and Complex Stimuli in Electric Hearing", Annals of Otology, Rhinology & Laryngology, vol. 104 (9), pp. 235-238.

Overstreet, Litvak, and Faltys inventors for AB-378U; U.S. Appl. No. 10/698,097; filed Oct. 31, 2003; entitled "Multi-Electrode Stimulation to Elicit Electrically-Evoked Compound Action Potential."

Overstreet inventor for AB-379U; U.S. Appl. No. 10/698,098; filed Oct. 31, 2003; entitled "Method and System for Generating a Cochlear Implant Program Using Multi-Electrode Stimulation to Elicit the Electrically-Evoked Compound Action Potential".

* cited by examiner

ENHANCED METHODS FOR DETERMINING ISO-LOUDNESS CONTOURS FOR FITTING COCHLEAR IMPLANT SOUND PROCESSORS

The present application claims the benefit of U.S. Provisional Patent Application Ser. No. 60/407,263, filed Aug. 30, 2002, which application is incorporated herein by reference in its entirety.

FIELD OF THE INVENTION

The present invention relates to cochlear implants, and more particularly to simplified methods for fitting cochlear implants that, in many instances, do not require patient feedback, clinician involvement, and/or measurement of minimum perception thresholds, and may be used with a variety of cochlear implant systems.

BACKGROUND OF THE INVENTION

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted through the patient's skin and then by a cable connection to an implanted multi-channel intra-cochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

A new, more sophisticated, class of cochlear implant, referred to as a bionic ear, is now available, providing patients with enhanced hearing performance. For example, Advanced Bionics® Corporation, of Sylmar, Calif., currently offers a cochlear implant which it refers to as the CII Bionic Ear® cochlear implant. Many features associated with the CII Bionic Ear® implant are described in U.S. Pat. No. 6,219,580, incorporated herein by reference. The added complexity of the CII Bionic Ear® cochlear implant includes higher numbers of channels, arbitrary simultaneous grouping, intra-phase gaps, binaural capabilities, and the like. The Bionic Ear implant contains advances in, e.g., internal memory banks, that enable it to send very detailed, high resolution sound signals to the auditory nerve. Such signals are delivered to the auditory nerve using a special electrode adapted to be inserted into the cochlea. A representative electrode usable with the CII Bionic Ear® is described in U.S. Pat. No. 6,129,753, also incorporated herein by reference.

Other improved features of cochlear implant systems are taught, e.g., in U.S. Pat. Nos. 5,626,629; 6,067,474; 6,157,861; 6,249,704; and 6,289,247, each of which is incorporated herein by reference.

The implantable cochlear stimulators described in at least the '629, '474, '861, '580, and '704 patents are able to selectively control the pulse width of stimulating pulses that are applied through the electrode array to the cochlea, and the frequency at which the stimulating pulses are applied.

When a cochlear prosthesis is first provided to a patient, it is necessary to initially "fit" or "adjust" the prosthesis. As used herein, it should be noted that the terms "fit", "adjust", "fitting", "adjusting", "program", or "programming" relate to making electronic or software programming changes to the prosthesis, as opposed to making physical or hardware changes. Proper fitting allows the prosthesis to better perform its intended function of helping the patient to sense sound.

As the art of cochlear stimulation has advanced, the implanted portion of the cochlear stimulation system, and the externally wearable processor (or speech processor) have become increasingly complicated and sophisticated. In addition, much of the circuitry previously employed in the externally wearable processor has been moved to the implanted portion, thereby reducing the amount of information that must be transmitted from the external wearable processor to the implanted portion. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the '629 patent. An improved fitting system is described in the '247 patent. The present invention is directed to simplified fitting systems that may be used with a variety of cochlear implants, such as those mentioned above.

The '247 patent describes representative stimulation strategies (a.k.a., speech processing strategies) that may be employed by a multichannel stimulation system. Such strategies define patterns of stimulation waveforms that are to be applied to the electrodes as controlled electrical currents. For instance, the speech processing strategy is used, inter alia, to condition the magnitude and polarity of the stimulation current applied to the implanted electrodes of the electrode array. If multiple electrode pairs exist, as is the case with a multichannel cochlear stimulator of the type used with the present invention, then the types of stimulation patterns applied to the multiple channels may be broadly classified as: (1) simultaneous stimulation patterns (substantially all electrodes receive current stimuli at the same time, thereby approximating an analog signal), or (2) sequential or non-simultaneous stimulation patterns (only one electrode receives a current pulse at one time). Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one where stimulation currents, either analog or pulsatile, are applied to the electrodes of two or more channels, but not necessarily all of the channels, at the same time.

Typically, when the fitting systems described in the '629 or '247 patents or the like are employed for multichannel stimulation systems, it is necessary to use thresholds derived from the measurement of psychophysically-determined comfort levels. That is, for each channel, a minimum threshold level is measured, typically referred to as a "T" level, which represents the minimum stimulation current which, when applied to a given electrode associated with the channel, produces a sensed perception of sound at least 50% of the time. In a similar manner, an "M" level is determined for each channel, which represents a stimulation current which, when applied to the given electrode, produces a sensed perception of sound that is moderately loud, or comfortably loud, but not so loud that the perceived sound is uncomfortable. These "T" and "M" levels, a.k.a., iso-loudness contours, are then used by the fitting software in order to properly map sensed sound to stimulation current levels that can be perceived by the patient as sound.

Disadvantageously, current methods for determining the "T" and "M" iso-loudness contours (or other levels) associated with each channel of a multichannel stimulation system is an extremely laborious, time-intensive, and imprecise task. Such determinations require significant time commitments on the part of the clinician, as well as the patient. In addition, for some patients, especially those whose responses are difficult to obtain, e.g., very young patients, these levels may be quite subjective and dependent on the experience of the clinicians performing the fitting procedure.

Current cochlear implant fitting techniques, in addition to requiring considerable clinical and patient time, have not been amenable to auto-fitting or patient self-programming. Furthermore, when fitting patients using high rate stimulation, where the statistical variability of T and M iso-loudness contours increases substantially, a new technique is necessary for performing optimal patient fittings.

SUMMARY OF THE INVENTION

The present invention simplifies the cochlear implant fitting process for various cochlear prostheses and stimulation strategies, including high rate stimulation strategies. For instance, patient self-programming is made possible with the present invention. The present invention also allows auto-fitting (particularly useful for very young patients and other patients from whom it is challenging to obtain feedback) using iso-neural response contours to predict iso-loudness contours and which can be linearly transposed. Furthermore, the present invention teaches linear transposition of M iso-loudness contours (or iso-neural contours) to determine T iso-loudness contours. In addition, with the present invention, wider pulse widths can be used to generate an iso-loudness contour whose shape can be used (via linear transposition) for the programming of high-rate, narrow pulse width stimulation.

Thus, the present invention provides fitting systems allowing one or combinations of:

1) patient self-programming (a.k.a., self-fitting),
2) fitting without determination of T-levels, and
3) fitting without patient feedback (a.k.a., auto-fitting).

These improvements are possible via, inter alia, the simplicity of the programming graphical user interface (GUI) provided by the present invention. For example, such a program could be placed on a handheld computer and the patient could setup the basic programming parameters prior to seeing their audiologist. Also, with the use of neural response imaging (NRI) strategies or the like, fitting becomes automatic, or at least comes closer to being automatic.

Due to the present invention, fitting is simplified, less time consuming, and potentially has improved results. For instance, the present invention may allow the patient to continually update their fitting, possibly without the aid of a clinician.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention.

At the outset, it is noted that, while the following describes the invention mainly in terms of the Clarion®, CII Bionic Ear®, and HiRes90K® cochlear implant systems, which cochlear implant systems are commercially available from Advanced Bionics® Corporation of Sylmar, Calif., the invention is not so limited. Rather, any multichannel cochlear implant system may benefit from the present invention. The CLARION®, CII Bionic Ear®, and HiRes90K® systems are referenced and described herein as examples of how the best mode of the invention may be implemented. As the CLARION®, CII Bionic Ear®, and HiRes90K® systems are not the subject of the invention, per se, many of the details associated with the CLARION®, CII Bionic Ear®, and HiRes90K® cochlear prostheses, including their electrodes, electrode arrays, implantable cochlear stimulators (ICSs), speech processors, and headpieces, are not presented herein, but may be found elsewhere, or are known in the art. For example, the CLARION® ICS is described, inter alia, in U.S. Pat. No. 5,603,726, which is incorporated herein by reference. As mentioned earlier, the CII Bionic Ear® system is described in U.S. Pat. No. 6,219,580.

Figure 1A:
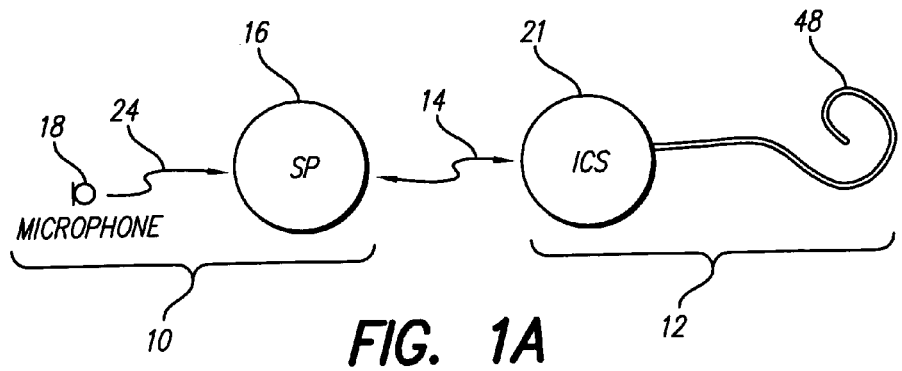
FIG. 1A shows an exemplary cochlear implant system.

Turning then to FIG. 1A, the present invention will be described. As seen in FIG. 1A, a cochlear stimulation system is shown that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes spaced along its length, e.g., sixteen electrodes, which electrodes are selectively connected to the ICS 21. The electrode array 48 may be substantially as shown and described in U.S. Pat. Nos. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and SP 16 are shown in FIG. 1A as linked together electronically through a suitable data or communications link 14. In some cochlear implant systems, e.g., the CLARION® system, SP 16 and microphone 18 comprise the external portion of the cochlear implant system and the ICS 21 and electrode array 48 comprise the implantable portion of the system. Thus, the data link 14 is a transcutaneous data link that allows power and control signals to be sent from SP 16 to ICS 21, and allows (in some configurations) data and status signals to be sent from ICS 21 to SP 16. The details of such communication link 14 are not important for purposes of describing the present invention.

In a typical Bionic Ear implant system, at least certain portions of the SP 16 are included within the implantable portion of the cochlear prosthesis, while other portions of the SP 16 remain in the external portion of the system. In general, at least microphone 18 and associated analog front end (AFE) circuitry will be part of the external portion of the system, and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of sensed acoustic signals) and/or power to be transmitted between the external portion and the implantable portion. In other configurations, both SP 16 and ICS 21 may be implanted within the patient, either in the same housing or in separate housings. If in the same housing, link 14 may be realized with a direct wire connection within such housing. If in separate housings, as taught, e.g., in U.S. Pat. No. 6,067,474, previously incorporated herein by reference, link 14 may be an inductive link using a coil or a wire loop coupled to the respective parts.

Microphone 18 senses acoustic signals and converts such sensed signals to corresponding electrical signals, and may thus be considered an acoustic transducer. The electrical signals are sent to SP 16 over a suitable electrical or other link 24. SP 16 processes these converted acoustic signals in accordance with a selected speech processing strategy in order to generate appropriate control signals for controlling ICS 21. Such control signals specify or define the polarity, magnitude, location (e.g., which electrode pair receives the stimulation current), and timing (e.g., when to apply the stimulation current to the electrode pair) of the stimulation current that is generated by the ICS. Such control signals combine to produce a desired spatiotemporal pattern of electrical stimuli in accordance with the desired speech processing strategy. Unlike prior art cochlear implant systems, the Bionic Ear system confines such control signals to circuitry within the implantable portion of the system, thereby avoiding the need to continually transmit such control signals across a transcutaneous link.

Speech processing strategies, as described earlier, define patterns of stimulation waveforms that are to be applied to the electrodes as controlled electrical currents. Non-simultaneous, fully simultaneous, and partially simultaneous strategies are known in the art, and examples or each type are given in U.S. Pat. No. 6,289,247, previously incorporated herein by reference. Below are brief descriptions of exemplary processing strategies.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsatile stimulation patterns are generally biphasic pulses, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity, having the same total charge, which charge is the product of stimulus current times duration of each pulse or phase.) For multichannel cochlear stimulators of the type used with the present invention, it is common to sample the acoustic signal at a rapid rate, and apply a biphasic stimulation pulse in sequence (i.e., non-simultaneously) to each of the pairs of electrodes of each channel in accordance with a specified pattern and cycle time, with the magnitude of the stimulation current being a function of information contained within the sensed acoustic signal at a given (e.g., the most recent) sample time. An example of such sequential, non-simultaneous stimulation pattern is a continuous interleaved sampler (CIS) strategy.

It is important to recognize that between the two extremes of fully simultaneous stimulation patterns (wherein analog stimulation currents are continuously applied to all channels, e.g., using the SAS strategy) and non-simultaneous pulsatile patterns (wherein biphasic pulses are applied in a specified sequence to all channels without time overlap, e.g., using the CIS strategy), there are a great number of other stimulation patterns that may be formulated. Such other simulation patterns may prove more efficacious for a given patient than either the SAS or CIS strategies. Thus, an important part of the fitting process is identifying which of several speech processing strategies is most beneficial for a given patient. The present invention assumes that an appropriate speech processing strategy has been identified, or can be easily identified. Additionally, it is assumed that selected electrodes may have been deactivated, e.g., based on electrode impedance measurements, to prevent diversion of current to broken electrodes.

Figure 1B:
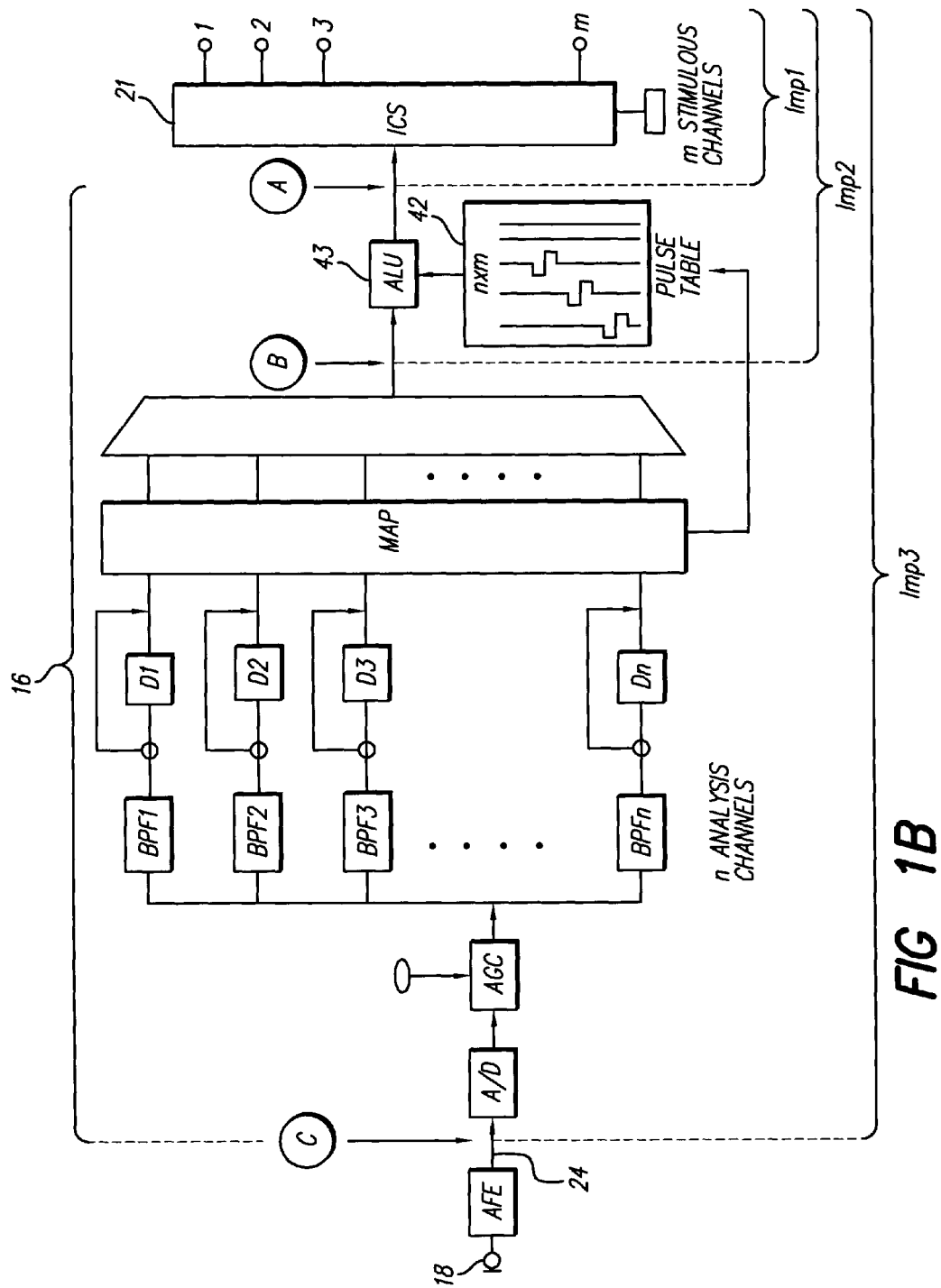
FIG. 1B is a block diagram of an exemplary cochlear system.

Turning to FIG. 1B, a partial block diagram of a representative bionic ear cochlear implant is shown. More particularly, FIG. 1B shows a partial functional block diagram of the SP 16 and the ICS 21 of an exemplary bionic ear cochlear implant system. FIG. 1B depicts the functions that are carried out by SP 16 and ICS 21. The electronic circuitry that is used to carry out these functions is not critical to the present invention. It should also be pointed out that the particular functions shown in FIG. 1B are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

A complete description of the partial functional block diagram of the bionic ear implant shown in FIG. 1B is found in U.S. Pat. No. 6,219,580, previously incorporated herein by reference. It is to be emphasized that the bionic ear functionality shown in FIG. 1B is only representative of one type of exemplary bionic ear implant, and is not intended to be limiting. The details associated with a given bionic ear implant are not critical to the present invention.

In the manner described in the '580 patent, the bionic ear implant functionally shown in FIG. 1B provides n analysis channels that may be mapped to one or more stimulus channels. That is, the system of FIG. 1B provides a multiplicity of channels, n, where the incoming signal is analyzed. The information contained in these n "analysis channels" is then appropriately processed, compressed and mapped in order to control the actual stimulus patterns that will be applied to the patient by the ICS 21 and its associated electrode array 48. The electrode array 48 includes a multiplicity of electrode contacts, connected through appropriate conductors, to respective current generators, or pulse generators, within the ICS. Through this multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient.

For instance, assume that n is not equal to m (n, for example, could be at least 20 or as high as 32 or more, while m may be, e.g., between 8 to 16). The signal resulting from analysis in the first analysis channel may be mapped to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site, and there may be several virtual stimulation channels created with different mapping ratios. This possibility of using different mapping schemes between n SP analysis channels and m ICS stimulation channels to thereby produce a large number of virtual and other stimulation sites provides a great deal of flexibility with respect to positioning the lead, electrodes, and/or neural excitation areas in a way that proves most beneficial to the patient.

Still with reference to FIG. 1B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp 1" serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also undesirable because the operating power increases.

In contrast to prior art systems, a bionic ear implant puts at least a portion of the speech processor 16 within the implanted portion of the system. For example, a bionic ear implant places the Pulse Table 42 and arithmetic logic unit (ALU) 43 inside the implanted portion, as indicated by the bracket labeled "Imp2" in FIG. 1B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

It is contemplated that future generations of bionic ear implant systems will incorporate more and more of the speech processor 16 within the implanted portion of the system. For example, a fully implanted speech processor 16 would incorporate all of the SP in the implanted portion, as indicated by the bracket labeled Imp3 in FIG. 1B. Such a fully implanted speech processor would offer the advantage that the data input into the system, i.e., the data stream that passes through point (C), would need only have rate commensurate with the input acoustic signal.

Figure 2A:
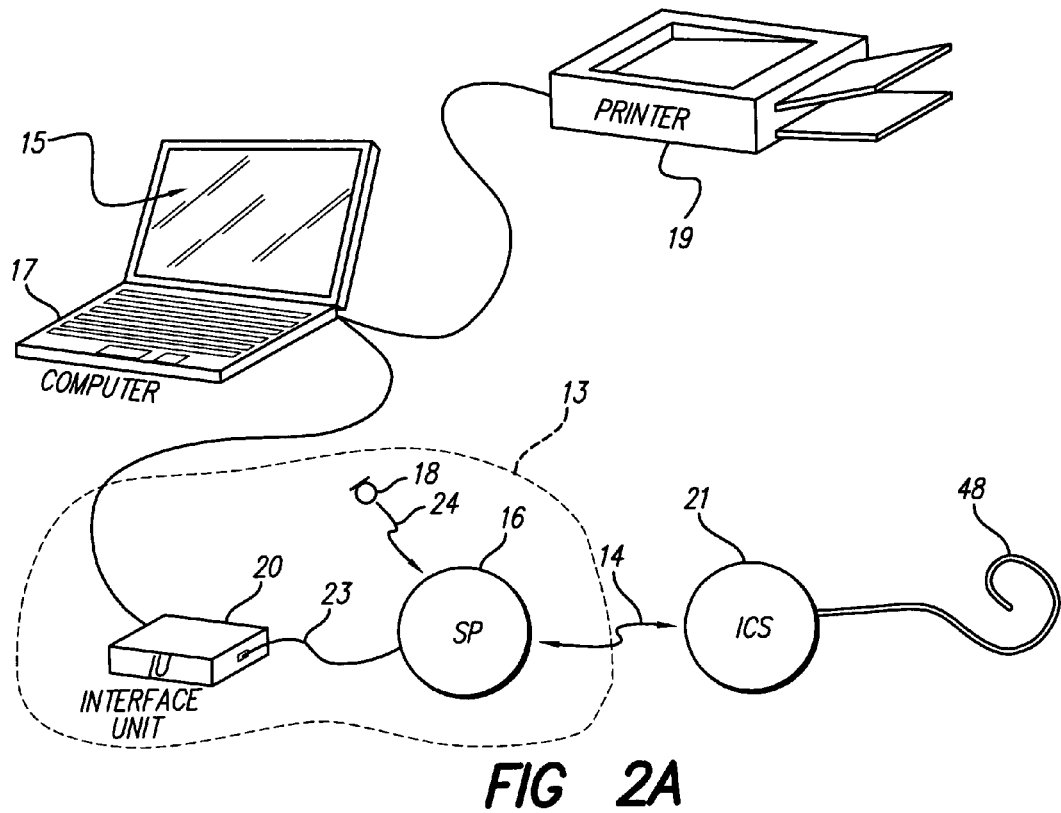
FIG. 2A depicts the elements of a typical fitting system used with a typical cochlear stimulation system.

Referring next to FIG. 2A, a block diagram of the components typically used to fit a patient with a cochlear implant system are shown. As seen in FIG. 2A, the implant system is as shown in FIG. 1A, and includes SP 16 linked to an ICS 21 with electrode array 48. A microphone 18 is also linked to SP 16 through a suitable communication link 24. A laptop, handheld, or palm computer 17, other type of computer, or equivalent device, is coupled to the speech processor 16 through an interface unit (IU) 20, or equivalent device. The type of linkage 23 established between SP 16 and IU 20 will vary, depending, for instance, on whether SP 16 is implanted. Any suitable communications link 23 may be used, as is known in the art, and thus the details of link 23 are not important for purposes of the present invention. It should be noted that for some applications, IU 20 may be included within computer 17 (e.g., as a communications interface already present within the computer, e.g., a serial port, or other built-in port, e.g., an IR port).

Computer 17, with or without IU 20 incorporated, provides input signals to SP 16 that simulate acoustical signals sensed by microphone 18 and/or provide command signals to SP 16. In some instances, the signals generated by computer 17 replace the signals normally sensed through microphone 18. In other instances, e.g., when testing the patient's ability to comprehend speech, the signals generated by computer 17 provide command signals that supplement the signals sensed through microphone 18.

The laptop computer 17 (or equivalent device) provides a display screen 15 on which selection screens, stimulation templates and other information may be displayed and defined. Such computer 17 thus provides the ability for the audiologist or other medical personnel, or even the patient, to easily select and/or specify a particular pattern of stimulation parameters that may be thereafter used, even if for just a short testing period, regardless of whether such stimulation pattern is simple or complex. Also shown in FIG. 2A is a printer 19 which may be connected to the computer 17, if desired, in order to allow a record of the selection criteria, stimulation templates and pattern(s) that have been selected and/or specified to be printed.

Figure 2B:
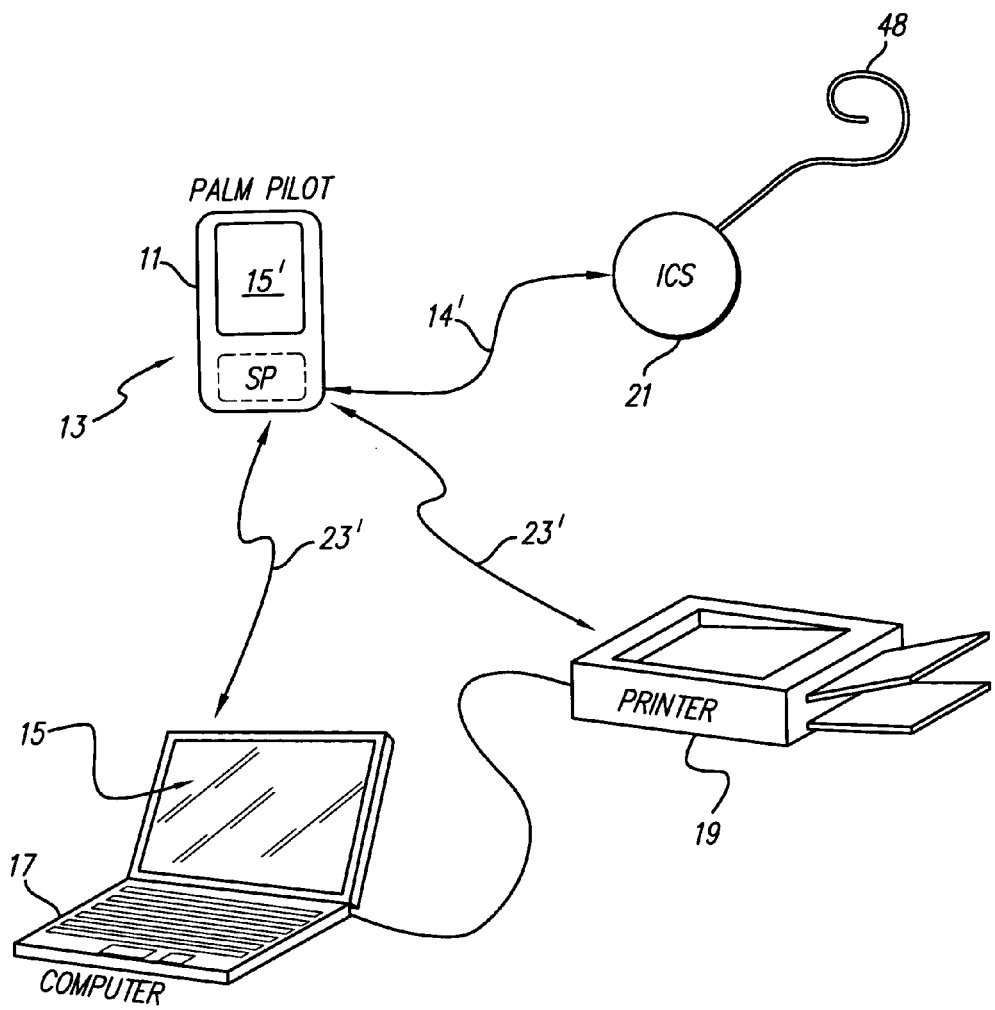
FIG. 2B depicts the elements of an alternate fitting system.

FIG. 2B illustrates a fitting system that may also/instead be used with the invention. In FIG. 2B, the ICS 21 is linked to a speech processor configured or emulated within a palm personal computer (PPC) 11, such as a Palm Pilot, or equivalent processor, commercially available, e.g., from Hewlett Packard. Such PPC 11 includes its own display screen 15' on which graphical and textual information may be displayed. In use, the PPC 11 may be linked, e.g., through a cable or an infrared link 23', to another computer 17, if necessary or desired. Typically, the functions of the SP and related devices are stored in a flashcard (a removable memory card that may be loaded into the PPC 11), thereby enabling the PPC 11 to perform the same functions of at least those elements encircled by the dotted line 13 in FIG. 2A. The PPC 11 is coupled to the ICS 21 through a suitable data/power communications link 14' and may also be linked, e.g., through a cable or an infrared link 23', to printer 19.

In traditional cochlear implant fittings, the value of T (which represents the minimum stimulation current which, when applied to a given electrode associated with the channel, produces a sensed perception of sound at least 50% of the time) is determined by the activation and testing of a single channel at a time using a sample signal. The intensity of this signal that meets the detection criterion is called the T level, as described earlier. This T level is then assumed to be appropriate for the system during "live speech" mode with all channels activated. However, the system has inherent noise, which is substantially different from single channel to live speech mode, resulting in a T mismatch. As a result, a given T iso-loudness contour is typically appropriate only for the signal used as the sample and only when the system noise is identical to what was present with the sample signal. Therefore, all the effort undertaken to determine the T iso-loudness contour may be wasted for many patients because the T level thus determined does not fit the live speech mode.

It has thus been proposed, in earlier patent applications of the present applicant, that T levels need not be measured for many, if not most, patients. Rather, the T level may be assumed to be zero or some other low value, e.g., some fraction of the measured M levels (which represents a stimulation current which, when applied to the given electrode, produces a sensed perception of sound that is moderately loud, or comfortably loud, but not so loud that the perceived sound is uncomfortable), such as $\frac{1}{10}$ of the M value for a given channel. By not having to measure individual T levels on each channel, significant time is saved during the fitting process.

Additionally, preliminary data indicate that T levels set in single channel psychophysics, painstakingly measured, overestimate the actual threshold required when all channels are running during live speech. Such an overestimation appears to penalize patient performance, particularly performance in noise. It has been empirically determined that for many patients, because T is apparently very close to the noise level, the T iso-loudness contour can simply be set to zero, or some other arbitrary level, thereby eliminating the need to go through the painstaking process of measuring T.

Preliminary data further indicate that when using simultaneous analog stimulation (SAS), the detectability of low level signals is enhanced such that certain patients may gain performance benefits without the use of T levels during live speech mode. This may similarly apply to other stimulation strategies, such as high rate stimulation, as described in U.S. Pat. No. 6,219,580, previously incorporated herein by reference.

Current cochlear implant fitting techniques, in addition to requiring considerable clinical and patient time, have thus far not been amenable to auto-fitting or patient self-programming. Furthermore, when fitting patients using high rate stimulation, where the statistical variability of threshold and comfort levels increases substantially, a new technique is necessary for performing optimal patient fittings. The present invention provides simplified cochlear implant fitting procedures for not only high rate stimulation strategies, but also for conventional stimulation strategies. The present invention also allows auto-fitting using iso-neural response contours to predict iso-loudness contours, which can be linearly transposed, i.e., with simple volume adjustments. In addition, with the present invention, wider pulse widths can be used to generate an iso-loudness contour whose shape can be used for the programming of high-rate, narrow pulse width stimulation.

Figures 3A, 3B:
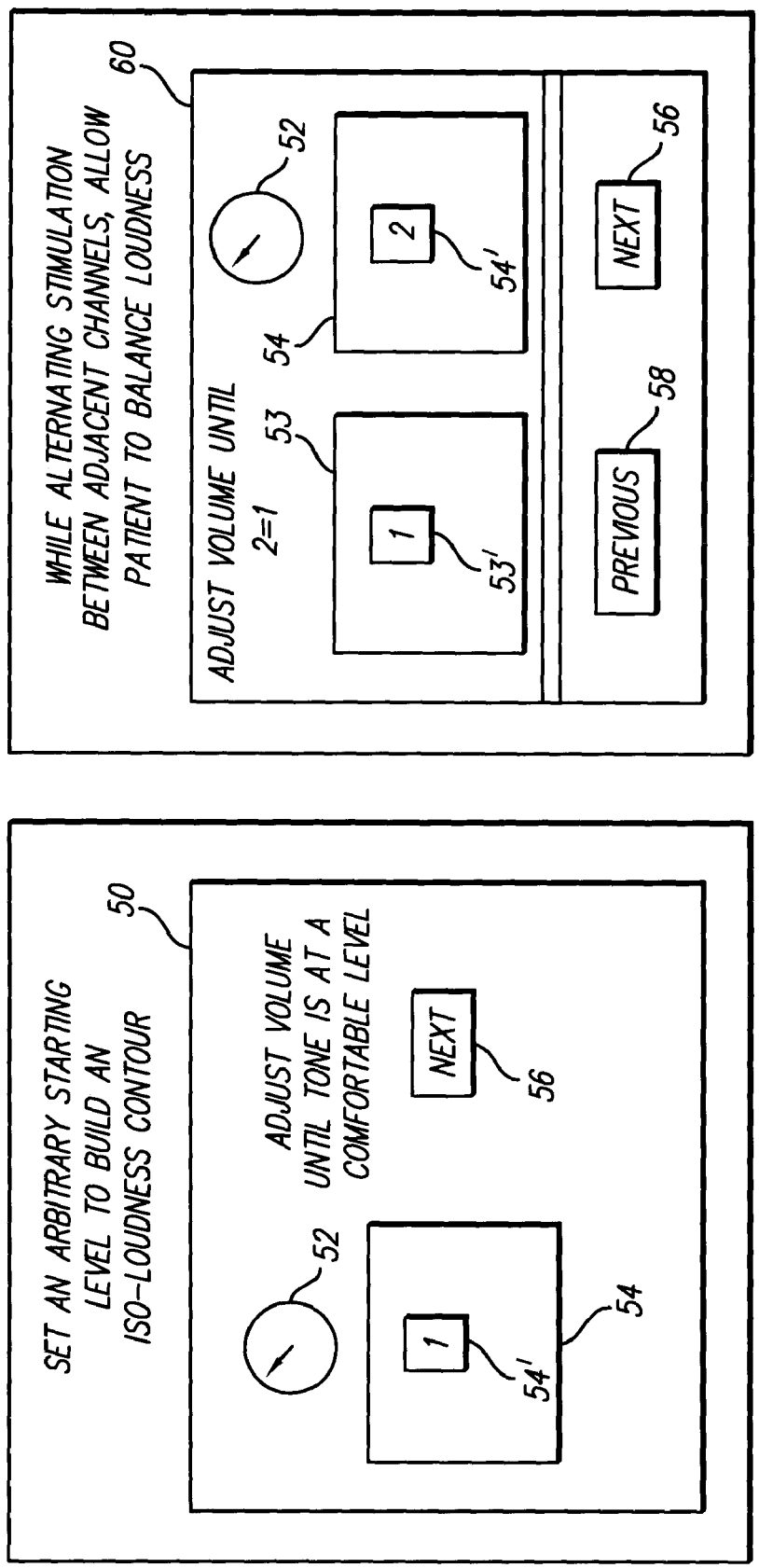
FIGS. 3A–3H show exemplary displays and workflow associated with aspects of a method of M iso-loudness contour determinations of the present invention.
Figure 3D:
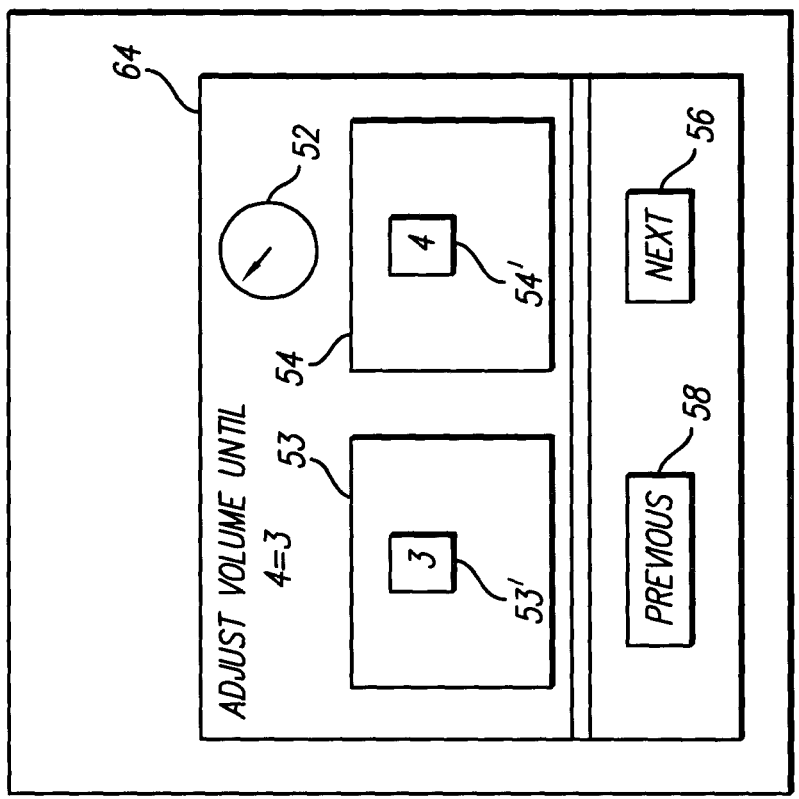

Turning now to FIGS. 3A–3H, a fitting method of the present invention will be described. These steps may be performed by the patient, in a self-programming session. As shown in FIG. 3A, the process starts with an arbitrary level applied to the first stimulation channel. This level may be preset by the clinician, or may start at zero or a very low level, so the possibility of over-stimulation is reduced. The patient is presented first screen 50 with instructions to "Adjust volume until tone is at a comfortable level" or similar words. Volume adjustment knob 52 appears with a channel indicator 54 for the channel being adjusted.

As this process will likely be performed on a desktop, laptop, handheld, palm, or other computer 17 (FIGS. 2A and 2B), a mouse or other pointing device may be used to "drag"

the volume up and down. Alternatively, if a touch-screen is used, a finger, pen, or other pointing device may be used. Other volume adjustment displays are possible, such as a slider-bar, a series of bars of increasing height, up and down arrows, or similar. Of course, a device with an actual knob or lever may also be used. Some patients, for instance those uncomfortable with computers, may find a specialized device with actual knobs, switches, levers, etc., easier to use, or a combination device may have actual knobs, etc. with a display screen that changes as needed. As such, "computer 17" may be any of such types of devices.

A tone may be heard when the volume adjustment device is released, and/or when channel selector 54' is selected. (To "select" a button or other item, a computer "button" or similar implement or icon may be clicked, pressed, etc., as is known in the computer art, or actual buttons, switches, etc., may be used.) Once the patient has adjusted channel 1 to a comfortable level, the patient selects, if necessary, "Next" (or similar) button 56.

Screen 60, shown in FIG. 3B, will then be presented to the patient. Volume knob 52 again appears with the channel indicator 54 for the channel to be adjusted, in this case, channel 2. The previous channel indicator 53 for the channel previously adjusted may also appear on the screen. The patient is instructed to "Adjust volume until 2=1" or similar language, meaning that the patient should manipulate the volume adjustment device 52 (knob, slider, arrows, etc.) until the volume of sound through channel 2 is similar to the volume of sound they heard through channel 1. In order to aid this process, the patient may alternately click on (or otherwise select) channel selector 54' and previous channel selector 53'. If desired, the patient may choose to return to the previous step by clicking (or otherwise selecting) Previous button 58, or similar. Once the patient has adjusted channel 2 to match the loudness of channel 1, the patient selects Next button 56.

Figure 3C:
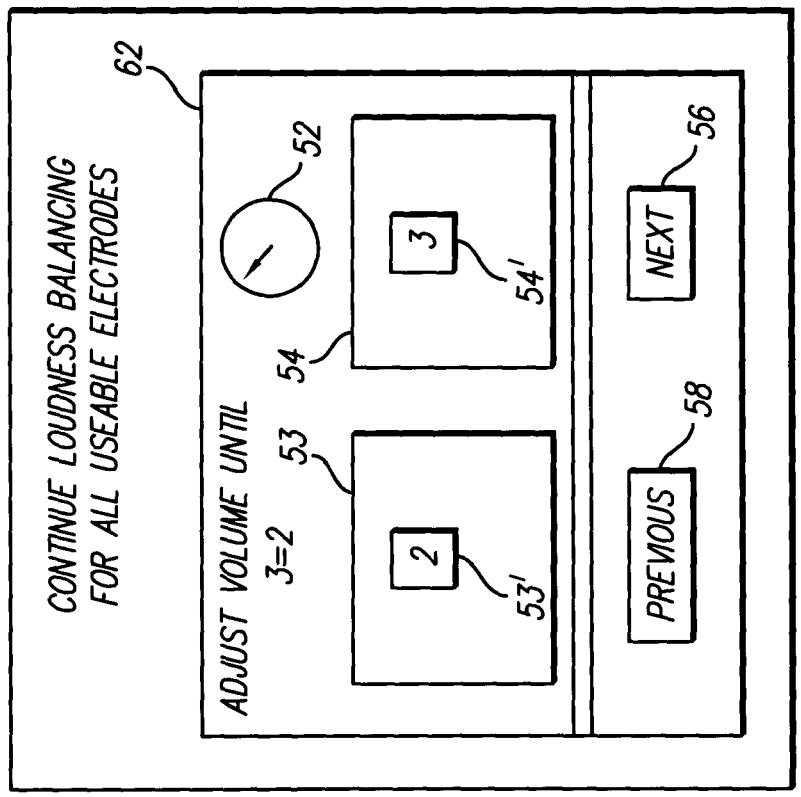
Figure 3F:
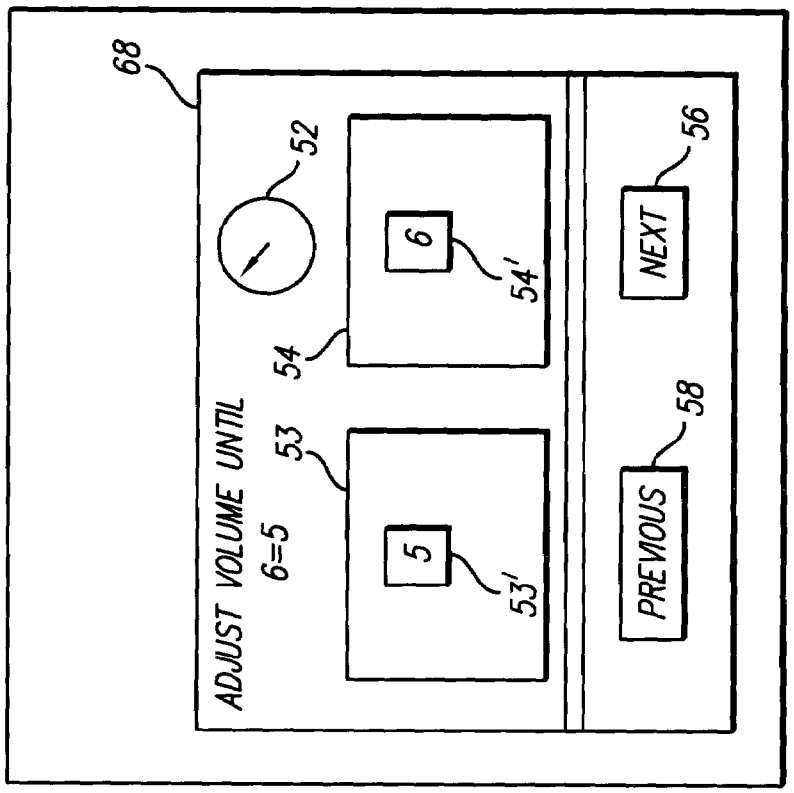
Figure 3E:
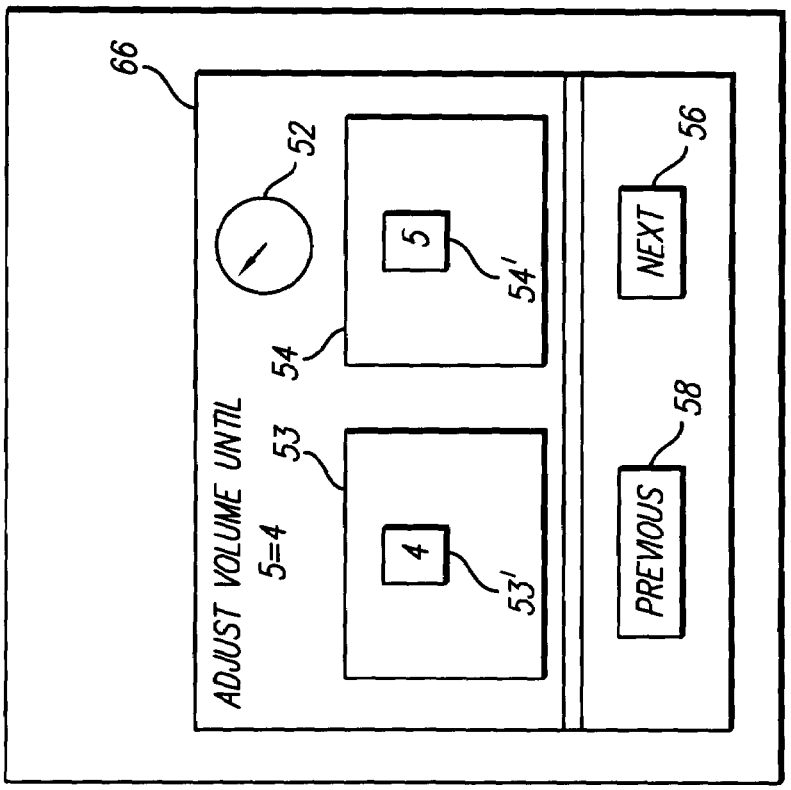
Figure 3H:
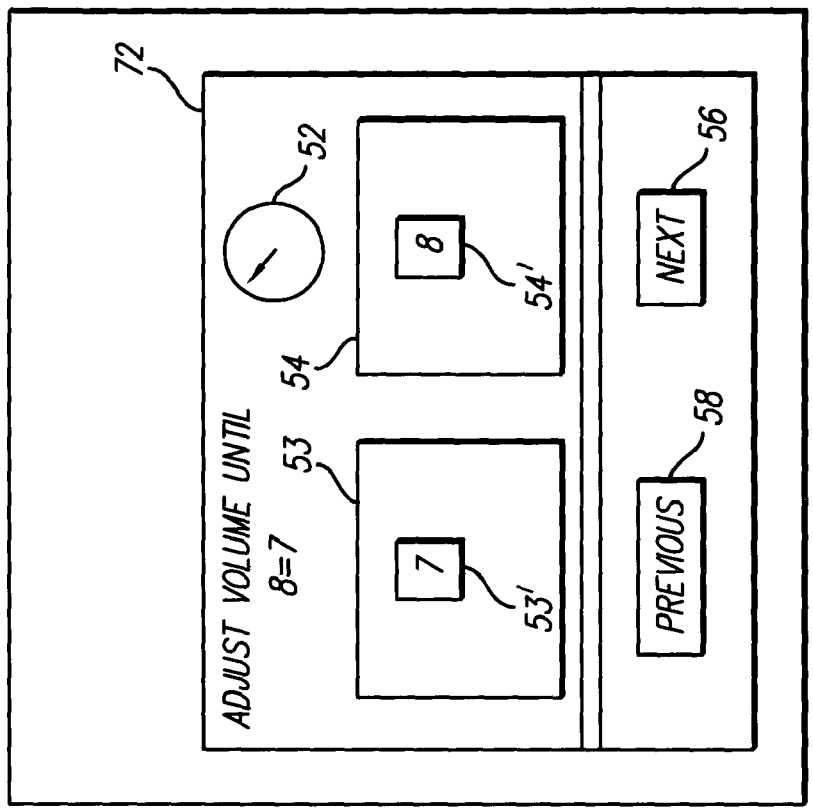
Figure 3G:
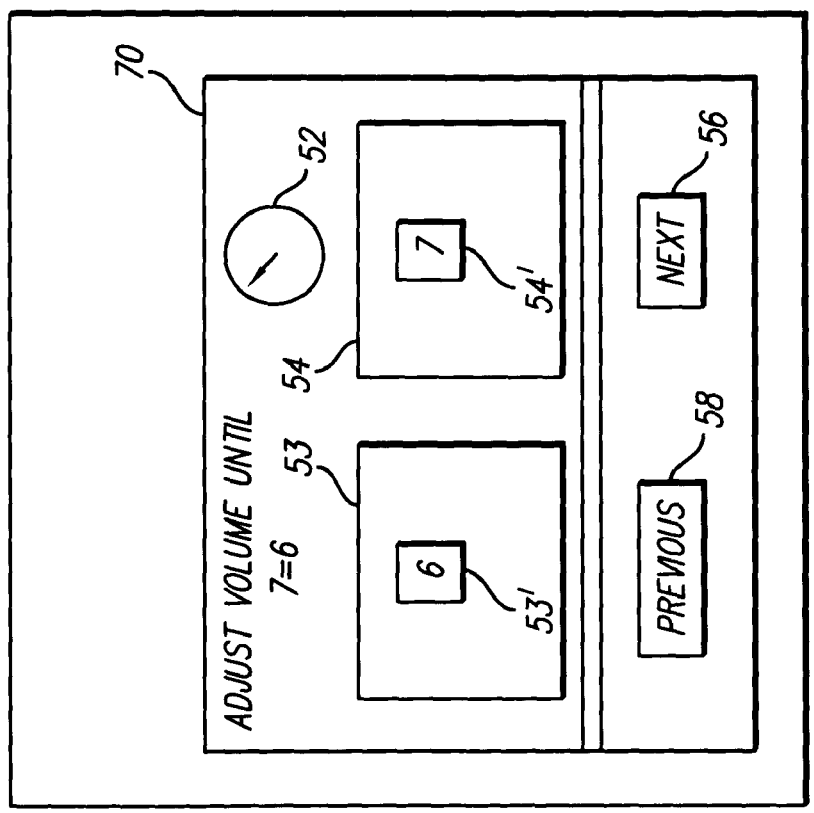

Screen 62, shown in FIG. 3C, will then be presented to the patient (unless the patient chose Previous button 58). Volume knob 52 again appears with the channel indicator 54 for the channel to be adjusted, in this case, channel 3. The previous channel indicator 53, in this case, shows channel 2. The patient is instructed to "Adjust volume until 3=2" or similar instruction. Channel selectors 53' and 54' allow the patient to select tones from either channel 2 or 3, respectively, in this case. Once again, the patient may choose to return to the previous screen by selecting the Previous button 58, or when satisfied, may select the Next button 56.

This process continues for all channels. For instance, if there are eight channels, the patient would continue through screens 64, 66, 68, 70, and 72, shown in FIGS. 3D, 3E, 3F, 3G, and 3H, respectively. After the last channel has been adjusted, for instance, the eighth channel in this example, screen 74, shown in FIG. 4A, will appear (or equivalent buttons, etc., will be available on a device). The patient is instructed to "Listen while each tone is played" or similar instruction. As each channel is intoned, the channel button 76 (which may or may not respond to clicking/pressing) for the active channel may light up or similar. A replay button or the like may be available so the patient may replay the tones before answering the question "Do each of the tones have the same loudness?" or similar. Once the patient is satisfied that they can answer this question, they may choose the yes button 78 or no button 79.

Figure 4B:
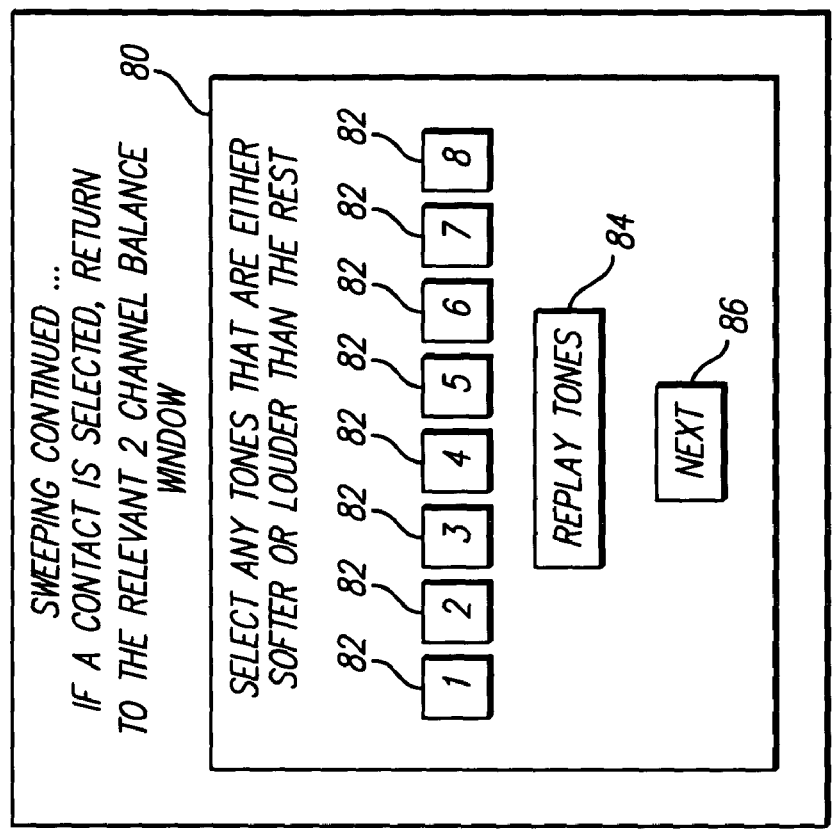
FIGS. 4A and 4B show exemplary displays and workflow associated with other aspects of M iso-loudness contour determinations of the present invention.
Figure 4A:
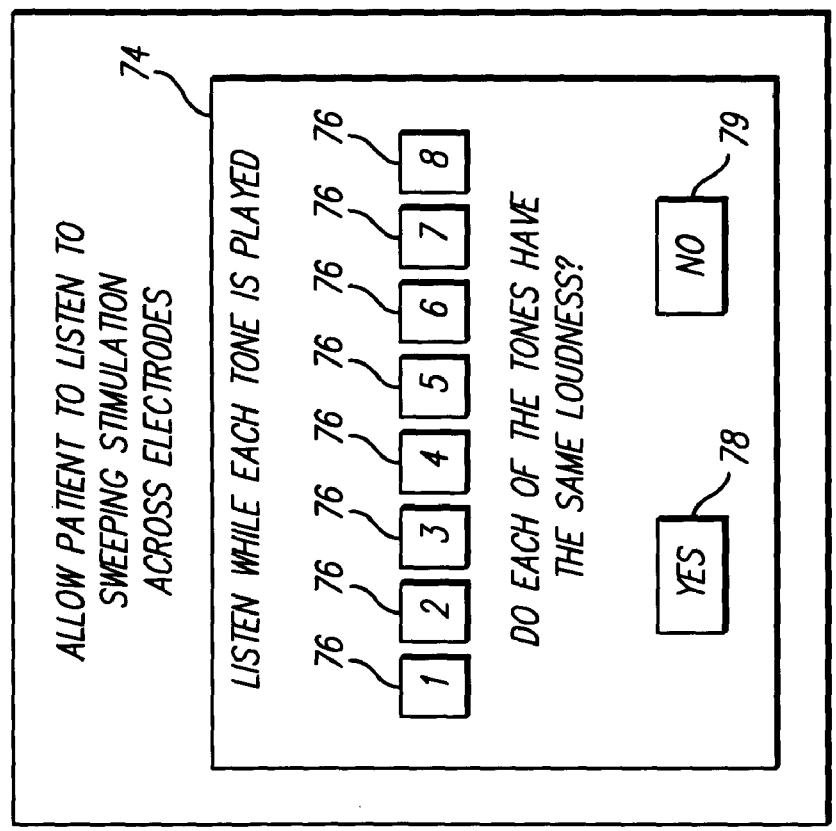

If the patient chooses no button 79, they will be directed to screen 80, shown in FIG. 4B. The patient may select a channel indicator 82 for any channel that seems either softer or louder than at least some of the others, or may choose the Replay tones button 84 until the patient is comfortable proceeding. If a channel indicator 82 is selected, the screen will return to one of screen 50, 60, 62, 64, 66, 68, 70, or 72, allowing the patient to adjust the chosen channel as described earlier. In this case, the Next button 56 or an additional button, such as a return button, may be available to return the patient to screen 74.

Figure 5:
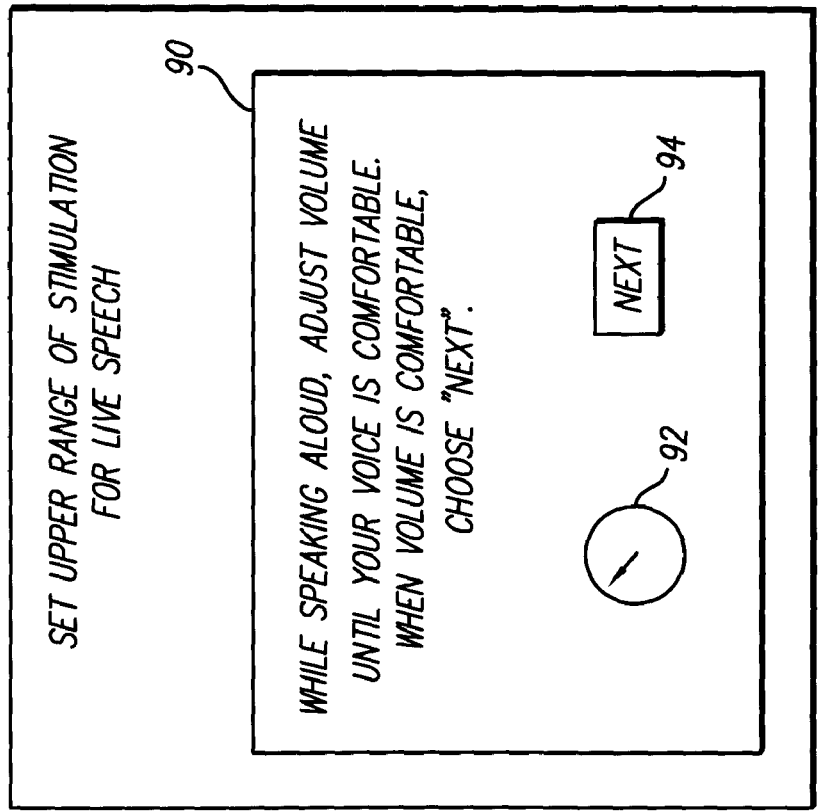
FIG. 5 shows an exemplary display associated with an optional aspect of a method of M iso-loudness contour determination of the present invention.

While at screen 74, if the patient chooses the yes button 78, or when the Next button 86 on screen 80 is chosen, screen 90, shown in FIG. 5, may appear (but may not be necessary or desired). The patient is instructed: "While speaking aloud, adjust volume until your voice is comfortable. When volume is comfortable, choose 'Next'." The volume may be adjusted in various ways as described earlier, such as with knob 92. This procedure ensures that the previously determined levels are appropriate for the patient's own speech. The earlier determined levels may be adjusted down or up based on this result. The Next button 94 may take the patient to a "fitting completed" screen, if desired, where the patient may have the option to repeat the process. In such a case, the results and choices from the earlier completed procedures may be retained or saved, and possibly used as starting points for subsequent fittings. Additionally or alternatively, results from multiple fitting procedures may be combined, as appropriate, to arrive at the values used by the cochlear implant. This completes one method of the present invention for determining the M iso-loudness contour.

Alterations may be made to the above procedures for determining the M iso-loudness contour, and still be encompassed by the present invention. For instance, rather than using tones to facilitate the comparisons of one channel to another, various other sounds may be used, such as a variety of types of noise, the patient's own speech, the clinician's speech, prerecorded speech by one or more people, and so on. In addition, there may be more or less channels included in the testing, depending on the cochlear implant configuration, whether virtual channels are available, and how many virtual channels are available. Additional or fewer screens, similar to those described above, would be used for more or less channels (actual and virtual), as needed. Furthermore, since iso-loudness contours are generally smooth curves, it is an option to "skip" some channels during the comparison, for instance, every other channel (actual or virtual), and extrapolate the curve for the skipped channels. This would speed the contour determination process. As described elsewhere herein, since the patient may be allowed to perform this procedure at any time, thereby potentially improving their iso-loudness contours and implant performance, there may be an option(s) allowing the patient and/or clinician to determine the specificity of a given procedure (e.g., whether to include virtual channels or to skip channels in a given procedure).

Figure 6A:
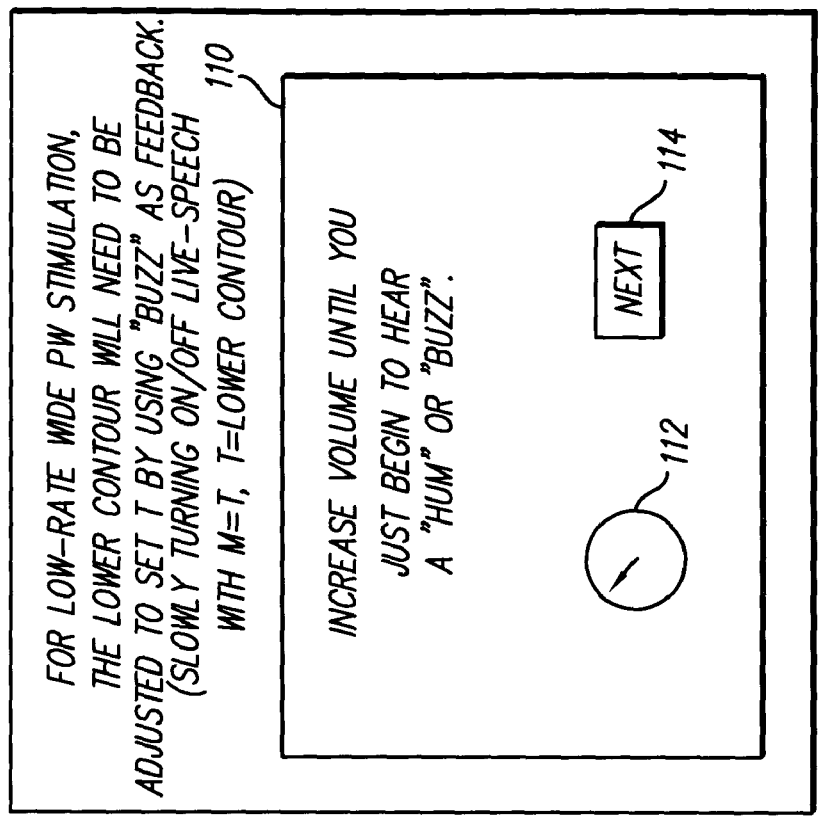
FIGS. 6A and 6B depict exemplary screen displays associated with a method of T iso-loudness contour determination of the present invention.
Figure 6B:
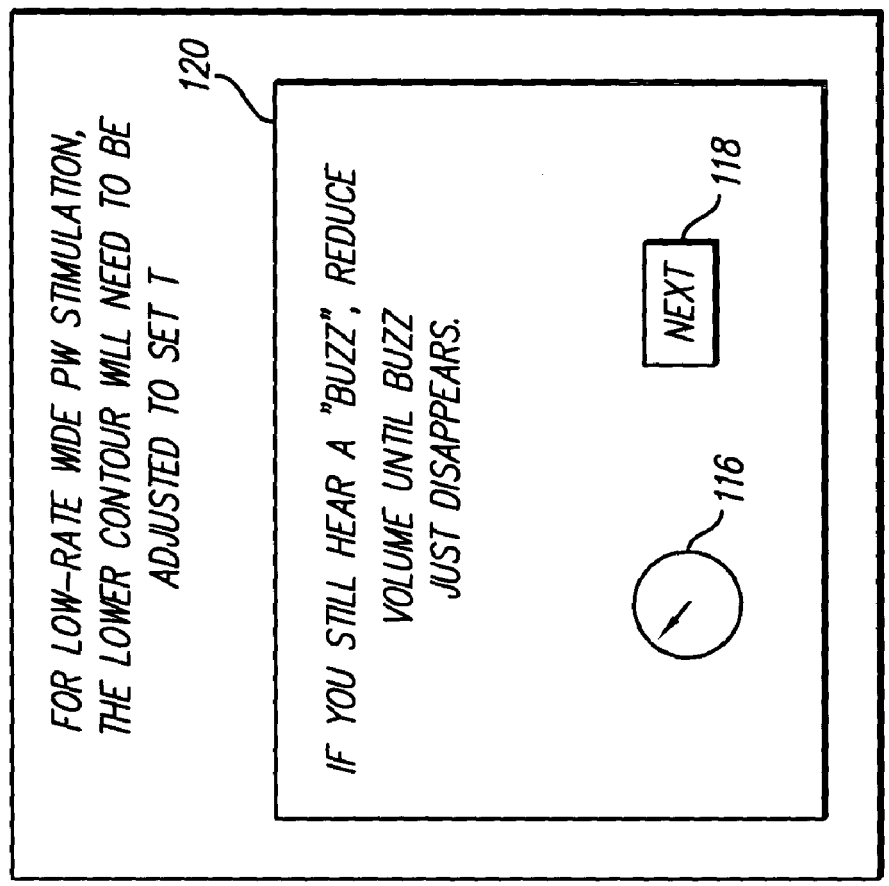

When necessary or desired, screens 110 and 120 (FIGS. 6A and 6B) will be used. As seen in FIG. 6A, these adjustments are most useful for low-rate, wide pulse width stimulation (such as CIS and MPS stimulation strategies). These screens are used to set the threshold iso-loudness contour T using a "buzz" or "hum" or similar as feedback. At screen 110, the patient is instructed to "Increase volume until you just begin to hear a 'hum' or 'buzz'" or the like. As described above, the patient may adjust the volume in various ways, such as with knob 112. When the patient is satisfied, they may choose Next button 114 to proceed to screen 120. The patient is then instructed "If you still hear a "buzz," reduce volume until buzz just disappears." The volume is again adjusted with knob 116 or equivalent. When the patient is satisfied, they may choose the Next button 118.

As above, the Next button 118 may take the patient to a "fitting completed" screen, where the patient may have the option to repeat part or all of the fitting process. Alternatively, screens 110 and 120 may repeat a given or optional number of times. The earlier completed procedures may be retained or saved, and possibly used as starting points for subsequent fitting procedures. In addition or alternatively, results from multiple fitting procedures may be combined, as appropriate, to arrive at the values used by the cochlear implant.

The above procedure for determining the T iso-loudness contour may be performed on a single channel. Once the difference between the M and T levels for that one channel is known, the earlier-determined M iso-loudness curve is shifted the amount of that difference and set as the T contour. In other words, it is proposed that the T iso-loudness contour follows the same iso-curve as the M iso-loudness contour. As a result, the M curve need only be shifted to a lower level by the appropriate amount, which may be determined by measuring the difference between the M and T level at one channel. Of course, if desired, the T level may be measured at more than one channel, and the software may allow the user to determine which channel(s) to measure.

Thus, it is unnecessary to measure psychophysical threshold levels (lower level T iso-loudness contours) on a channel-by-channel basis (or at all, for some stimulation strategies). This greatly reduces the time demands associated with the cochlear fitting process. In addition, by avoiding such measurements for some stimulation strategies, the patient's performance potentially improves. (As mentioned earlier, with high-rate stimulation strategies, it may not be necessary or desirable to use a T-level or a measured T level. This is due to the wider dynamic range strategies such as SAS and High Rate. Instead, the T contour may be set to zero or some low value. It may still be necessary or desired with lower rate, wide pulse width strategies, such as CIS and MPS, to more closely determine and set the T levels since inaccuracies would have a greater impact when the dynamic range is more narrow. In some cases, it may even be necessary or desired to set T levels with a more traditional approach, one channel at a time, or with a method like the comparison method above.

In any case, at least some stimulation strategies will allow the M iso-loudness contour to be linearly transposed to a lower level in order to obtain the T iso-loudness contour. The M iso-loudness contour may be obtained as taught above, or by other methods. For instance, NRI (neural response imaging) or EABR (evoked auditory brainstem response) may be used to obtain an iso-neural contour. (NRI measurements are described, e.g., in U.S. Pat. No. 6,157,861, previously incorporated herein by reference, and U.S. Pat. No. 6,195,585, incorporated herein by reference.) These iso-neural response curves may appear at any level. However, with the present invention, this is irrelevant. The iso-neural curve need only be linearly transposed to the M level and, if needed or desired, to the T level (each measured, for instance, on only one or few channels). In other words, the M iso-loudness curve (and potentially the T curve as well) can be predicted by an iso-neural curve, such as from NRI or EABR, since they follow the same iso-curve. Furthermore, if the M iso-loudness curve is known—psychophysically determined as with the method above, or predicted with an iso-neural curve—the T iso-loudness curve can be predicted, since, at least for some stimulation strategies, they follow the same iso-curve. Therefore, in any of these cases, the different levels of the curves need only be determined with a single channel (although more than one may also be used), and the difference used as the amount and direction of linear transposition.

In addition, with the present invention, wider pulse widths can be used to generate an iso-loudness contour whose shape can be used for the programming of high-rate, narrow pulse width stimulation. Since single channel measurements at high rates and at narrow pulse widths are made difficult by possible adaptation and shallow loudness growth (resulting in poor loudness perception), the relative shape of the upper level iso-loudness contour (most comfortable level M) may also or instead be determined at a wider pulse width. For instance, contours determined with pulse widths of about 30 µs or about 35 µs or even about 75 µs may be used to predict the contours at about 10 µs or about 20 µs. The iso-curves so determined may then be linearly scaled, if needed (e.g., due to channel summation), to give the patient the appropriate volume.

Thus, the present invention provides, inter alia, for SAS and High Rate stimulation strategies, that only one contour is required and can be obtained with NRI, EABR, or by a psychophysically determined loudness-balancing task. For stimulation requiring a threshold setting, such as CIS, MPS, and other low rate, wide pulse width stimulation strategies, an iso-loudness or iso-neural response contour can be linearly transposed to a lower level, for instance during live-speech with M=T until the patient no longer reports the sensation of a "buzz" or "hum". As shown above, iso-contours are much easier to obtain than maximal comfort levels or threshold levels.

While the invention herein disclosed has been described by means of specific embodiments and applications thereof, numerous modifications and variations could be made thereto by those skilled in the art without departing from the scope of the invention set forth in the claims.

What is claimed is:

1. A method of fitting a cochlear implant, the cochlear implant having an electrode array with multiple electrode contacts through which a pulsatile stimulation waveform having a pulse rate and a pulse width may be applied to the cochlea of the patient; and wherein the fitting method builds an M iso-loudness contour and determines a T iso-loudness contour, the method comprising:
   a) setting a starting sound level to build an iso-loudness contour;
   b) setting volume on a first channel until the sound is at a predetermined level;
   c) adjusting volume on a second channel until the volume of sound on the second channel is similar to the volume of sound on the first channel; then
   d) setting the next channel to result in the same sound volume determined for the previous channel;
   e) repeating step (d) for each available channel until the stimulation level for the last channel is adjusted, and the M iso-loudness contour is built; and
   f) picking one channel and determining the volume level of that one channel; and
   g) generating a T-iso-loudness contour by determining the difference in the volume level measured for the one channel in step f) and the M volume level found previously for that channel and linearly shifting the M iso-loudness contour by the determined difference in volume level.

2. The method of claim 1 wherein the starting sound level is no sound.

3. The method of claim 1 wherein the sound includes a tone or tones.

4. The method of claim 1 wherein the sound includes noise.

5. The method of claim 1 wherein the sound includes speech.

6. The method of claim 1 wherein the predetermined level is a comfortable level.

7. The method of claim 1 wherein the predetermined level is a threshold level.

8. The method of claim 1 wherein at least one channel is a virtual channel.

9. The method of claim 1 wherein at least one channel is skipped.

10. A method of fitting a cochlear implant, the cochlear implant having an electrode array with multiple electrode contacts through which a pulsatile stimulation waveform having a pulse rate and a pulse width may be applied to the cochlea of the patient; and wherein the fitting method sets an iso-loudness contour from an iso-neural response contour, the method comprising:
   determining an iso-neural response contour; and
   linearly transposing the iso-neural contour to set an iso-loudness contour.

11. The method of claim 10 further comprising using at least one of neural response imaging and evoked auditory brainstem response to determine the iso-neural response contour.

12. The method of claim 10 further comprising
   determining an M level for at least one channel;
   determining a difference between the iso-neural level and the M level for the at least one channel; and
   linearly transposing the iso-neural contour by the amount of the difference to set the iso-loudness contour.

13. The method of claim 10 wherein the iso-loudness contour is an M iso-loudness contour.

14. The method of claim 10 wherein the iso-loudness contour is a T iso-loudness contour.

15. A method of fitting a cochlear implant, the cochlear implant having an electrode array with multiple electrode contacts through which a pulsatile stimulation waveform having a pulse rate and a pulse width may be applied to the cochlea of the patient; and wherein the fitting method uses at least two iso-loudness contours, the method comprising:
   determining a first iso-loudness response contour; and
   linearly transposing the first iso-loudness contour to set a second iso-loudness contour.

16. The method of claim 15 wherein the first iso-loudness contour is an M iso-loudness contour.

17. The method of claim 16 wherein the second iso-loudness contour is a T iso-loudness contour.

18. The method of claim 15 further comprising:
   determining a difference between the first iso-loudness contour level and the second iso-loudness contour using at least one channel; and
   linearly transposing the first iso-loudness contour by the amount of the difference to set the second iso-loudness contour.

19. A method of fitting a cochlear implant, the cochlear implant having an electrode array with multiple electrode contacts through which a pulsatile stimulation waveform having a pulse rate and a pulse width may be applied to the cochlea of the patient; and wherein the fitting method determines an iso-loudness contour, the method comprising:
   setting pulse width to about 30 µs to about 75 µs;
   determining an iso-loudness contour with the set pulse width; and
   linearly transposing the iso-loudness contour for use with pulse widths of about 10 µs to about 20 µs.

20. The method of claim 19 further comprising:
   determining a difference between the iso-loudness contour level with the set pulse width and a comfortable volume for pulse widths of about 10 µs to about 20 µs; and
   linearly transposing the iso-loudness contour by the amount of the difference.

* * * * *